(12) United States Patent
Sablone

(10) Patent No.: US 9,301,882 B2
(45) Date of Patent: Apr. 5, 2016

(54) PROCESS FOR PRODUCING SANITARY ARTICLES THAT CAN BE WORN AS A PAIR OF PANTS, AND CORRESPONDING ARTICLE

(75) Inventor: Gabriele Sablone, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 767 days.

(21) Appl. No.: 13/578,898

(22) PCT Filed: Feb. 8, 2011

(86) PCT No.: PCT/IB2011/050524
§ 371 (c)(1),
(2), (4) Date: Aug. 14, 2012

(87) PCT Pub. No.: WO2011/101773
PCT Pub. Date: Aug. 25, 2011

(65) Prior Publication Data
US 2012/0304363 A1 Dec. 6, 2012

(30) Foreign Application Priority Data
Feb. 16, 2010 (IT) .............................. TO2010A0113

(51) Int. Cl.
*A61F 13/15* (2006.01)
*B32B 38/04* (2006.01)
(Continued)

(52) U.S. Cl.
CPC ..... *A61F 13/15756* (2013.01); *A61F 13/15747* (2013.01); *A61F 13/5622* (2013.01); *B32B 38/0004* (2013.01); *B32B 38/10* (2013.01); *Y10T 156/1049* (2015.01); *Y10T 156/1051* (2015.01); *Y10T 156/1077* (2015.01); *Y10T 156/1092* (2015.01); *Y10T 156/1097* (2015.01)

(58) Field of Classification Search
None
See application file for complete search history.

(56) References Cited

U.S. PATENT DOCUMENTS

5,399,219 A * 3/1995 Roessler ........... A61F 13/15756
156/229
6,572,595 B1 6/2003 Klemp et al.
(Continued)

FOREIGN PATENT DOCUMENTS

EP 1 941 853 7/2008
EP 1 941 853 A1 7/2008
(Continued)

OTHER PUBLICATIONS

Apr. 8, 2010 certified U.S. Appl. No. 61/212,011, filed Apr. 6, 2009, "Methods and Apparatus for Application of Nested Zero Waste Ear to Traveling Web", McCabe et al., 45 pages.
(Continued)

*Primary Examiner* — Linda L Gray
(74) *Attorney, Agent, or Firm* — Nixon & Vanderhye P.C.

(57) ABSTRACT

Sanitary articles (1) that can be worn as a pair of pants, said articles (1) comprising a central body (2), which can be set around the crotch region of the user, said central body (2) extending in a longitudinal direction (X1) between two opposite ends, and at least one pair of side panels (3), which are connected to one of the ends of the central body (2) and extend on opposite sides of said central body (2) to define at least in part the waistband of the article (1). The side panels (3) are connected to the central body (2) while they are in a folded condition. The aforesaid panels are preferentially obtained in a folded condition, with the distal edge (7) set in the proximity of the proximal edge (6).

16 Claims, 9 Drawing Sheets

(51) Int. Cl.
*A61F 13/56* (2006.01)
*B32B 38/00* (2006.01)
*B32B 38/10* (2006.01)

(56) References Cited

U.S. PATENT DOCUMENTS

| | | | |
|---|---|---|---|
| 6,994,761 | B2 | 2/2006 | Klemp et al. |
| 2004/0016499 | A1* | 1/2004 | Miyamoto ........ A61F 13/15756 156/66 |
| 2005/0119634 | A1 | 6/2005 | Fletcher et al. |
| 2005/0230024 | A1 | 10/2005 | McCabe |
| 2008/0009816 | A1 | 1/2008 | Kenmochi et al. |
| 2010/0065199 | A1 | 3/2010 | Harmung et al. |

FOREIGN PATENT DOCUMENTS

| | | |
|---|---|---|
| EP | 2 057 975 | 5/2009 |
| EP | 2 057 975 A1 | 5/2009 |
| EP | 2 238 955 A1 | 10/2010 |
| JP | 2000-506047 | 5/2000 |
| WO | WO97/32556 | 9/1997 |
| WO | WO 2008/141834 | 11/2008 |
| WO | WO 2010/136933 A1 | 12/2010 |
| WO | WO 2011/101773 A1 | 8/2011 |

OTHER PUBLICATIONS

Italian Application No. TO2010A000113, filed Feb. 16, 2010 (with English translation of claims and Figs. 1-13).
International Search Report for PCT/IB2011/050524, mailed Jun. 15, 2011.
Written Opinion of the International Searching Authority for PCT/IB2011/050524, mailed Jun. 15, 2011.
Translation of JP 2000-506047.
European Patent Office Action dated May 28, 2013, from European Patent Application No. EP 11710310.1.

* cited by examiner

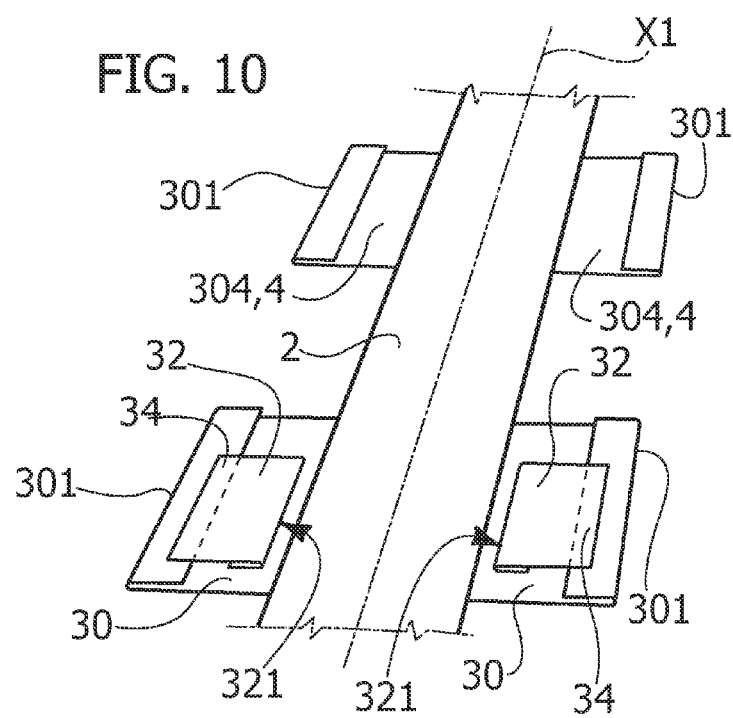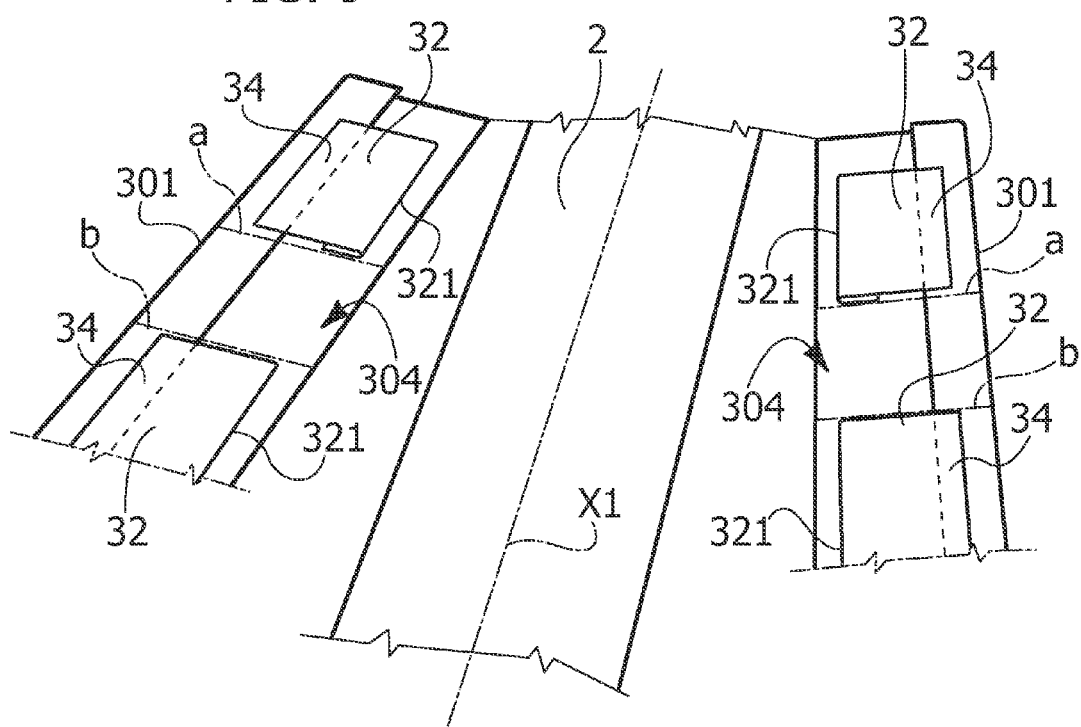

PROCESS FOR PRODUCING SANITARY ARTICLES THAT CAN BE WORN AS A PAIR OF PANTS, AND CORRESPONDING ARTICLE

This application is the U.S. national phase of International Application No. PCT/IB2011/050524, filed 8 Feb. 2011, which designated the U.S. and claims priority to IT Application No. TO2010A000113, filed 16 Feb. 2010, the entire contents of each of which are hereby incorporated by reference.

FIELD OF THE INVENTION

The present description relates to the production of sanitary articles that can be worn as a pair of pants.

In particular, the description relates to the production of sanitary articles comprising a central body, connected to which is, at one end at least, a pair of side panels.

DESCRIPTION OF THE PRIOR ART

Documents such as, for example, EP-A-1 941 853 describe processes for manufacturing sanitary articles that can be worn as a pair of pants and comprise:
- a central body, which can be set around the crotch region of the user, said central body extending in a longitudinal direction between two opposite ends; and
- at least one pair (and possibly two pairs) of side panels connected to one (and possibly to each) of the ends of said central body and extending on opposite sides of said central body to define at least in part the waistband of the article.

Said sanitary articles can be absorbent products that comprise, set in the central body, an absorbent element (core).

The side panels can also comprise an elasticated material, which is quite costly (or in any case of high quality) and of which it is in the interest of the manufacturer to minimize the waste.

The sanitary articles in question are designed both for use by newborn babies and small children, and
  to an ever-increasing extent—for use by incontinent adults.

In the context of use cited last, the requirements of production of so-called "bariatric" sanitary articles, i.e., ones designed for obese adults, are assuming increasing importance. In these cases, the articles are of considerable size: for instance, a central body of approximately one meter in length and approximately 90 cm in width, so as to reach circumferences of the waistband of the finished article even in the region of 180 cm.

In the production and packaging of articles such as ones designed for adults, the dimensions of the articles are such as to render critical execution of various operations of manipulation, for instance, application and folding of the side panels.

In addition to this, given the same geometry of the article, the possible waste of material is proportional to the dimensions of the article itself; consider, by way of example, the waste that may derive from the operation of cutting of the openings for passage of the user's legs: waste that is tolerable in articles of small dimensions may no longer be tolerable in articles of large dimensions, where the overall amount of material discarded can become significant and no longer acceptable in the case of costly or in any case high-quality materials.

The considerations set forth above must also be weighed in the light of the very high production rates (hundreds of articles per minute) that it is in any case desired to maintain.

Also at the level of the article in itself, in the case of articles of small dimensions, adaptation to the size of the user can be achieved with modest dimensional adjustments (for example, at the level of a slight variation of the position of fixing of the closing formations); in the case of articles of large dimensions, adaptation to the size of the user can instead require much larger dimensional adjustments (for example, at the level of variation of several centimeters), with the dual requirement of:
  on the one hand, making available, for instance, in the side panels, material such as to render optionally larger the article worn; and
  on the other hand, preventing, in an article worn that is more adherent, the possibility of there remaining tabs, creases, folds, etc. such as to prove bothersome for the person wearing the article.

OBJECT AND SUMMARY OF THE INVENTION

The object of the present invention is to provide a solution that will be able to overcome the critical aspects outlined above.

According to the invention, said object is achieved thanks to a process having the characteristics recalled in the ensuing claims.

The invention also regards an article that can be obtained following the aforesaid process.

The claims form an integral part of the technical teaching provided herein in relation to the invention.

Various embodiments apply not only to articles for incontinent adults, to which explicit reference has been made previously, but also to articles for newborn babies and small children.

Various embodiments envisage connecting the side panels to the central body of the article with the side panels in a folded condition.

Various embodiments envisage formation of the side panels in a folded condition.

In various embodiments, in the aforesaid folded condition the side panels have their distal edge situated in the proximity of the proximal edge.

BRIEF DESCRIPTION OF THE ANNEXED DRAWINGS

The invention will now be described purely by way of non-limiting example, with reference to the annexed drawings, in which.

Figure 11:
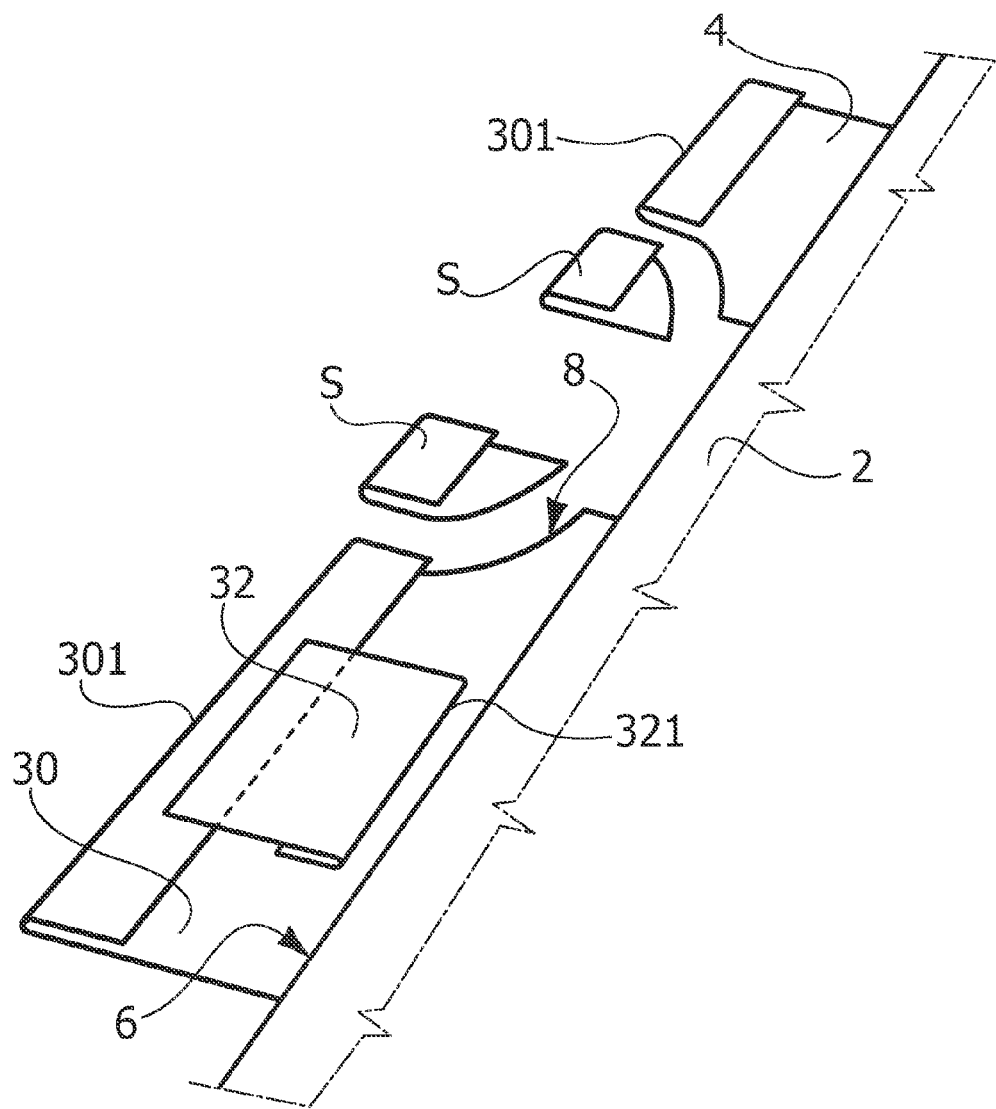
Figure 12:
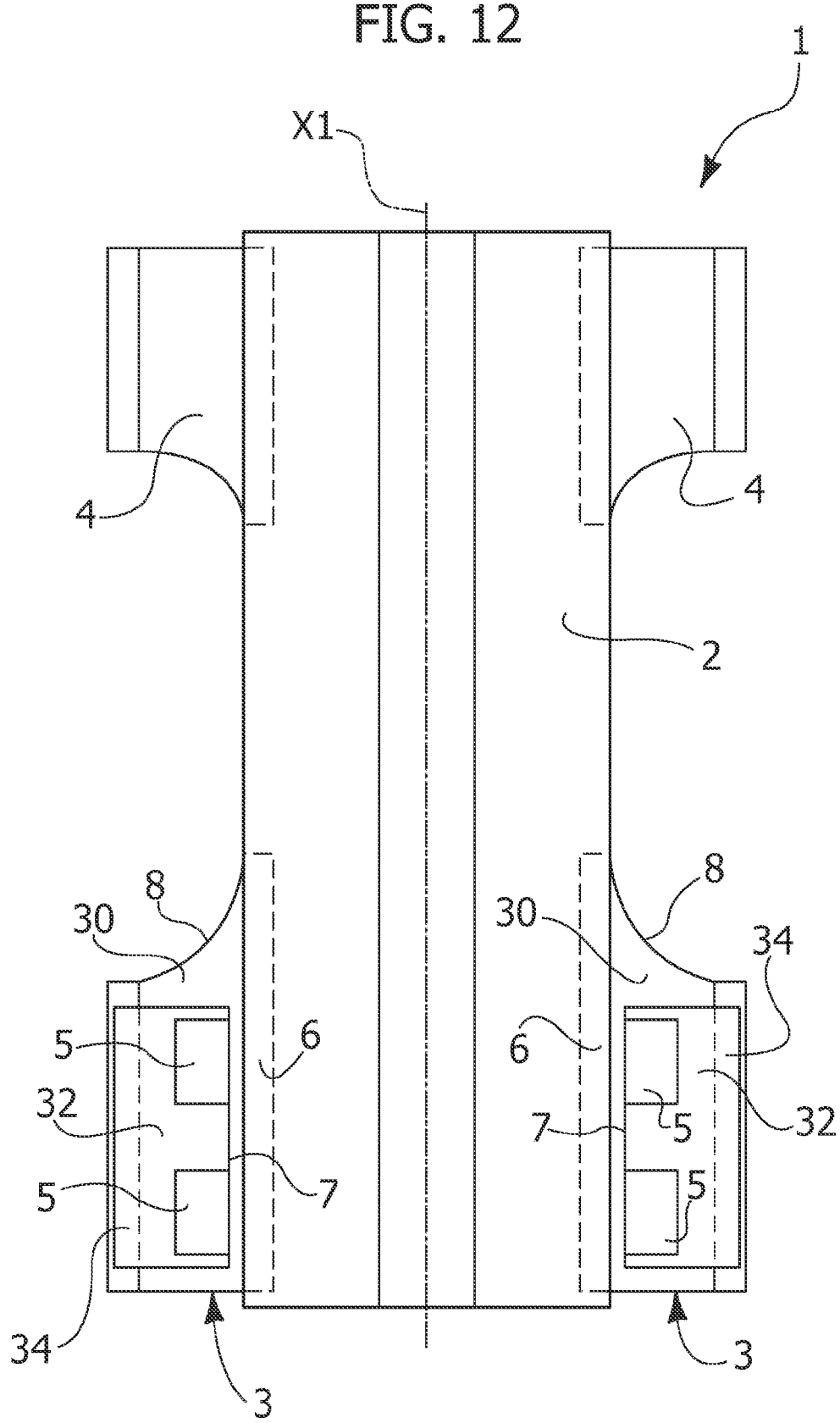
Figure 13:
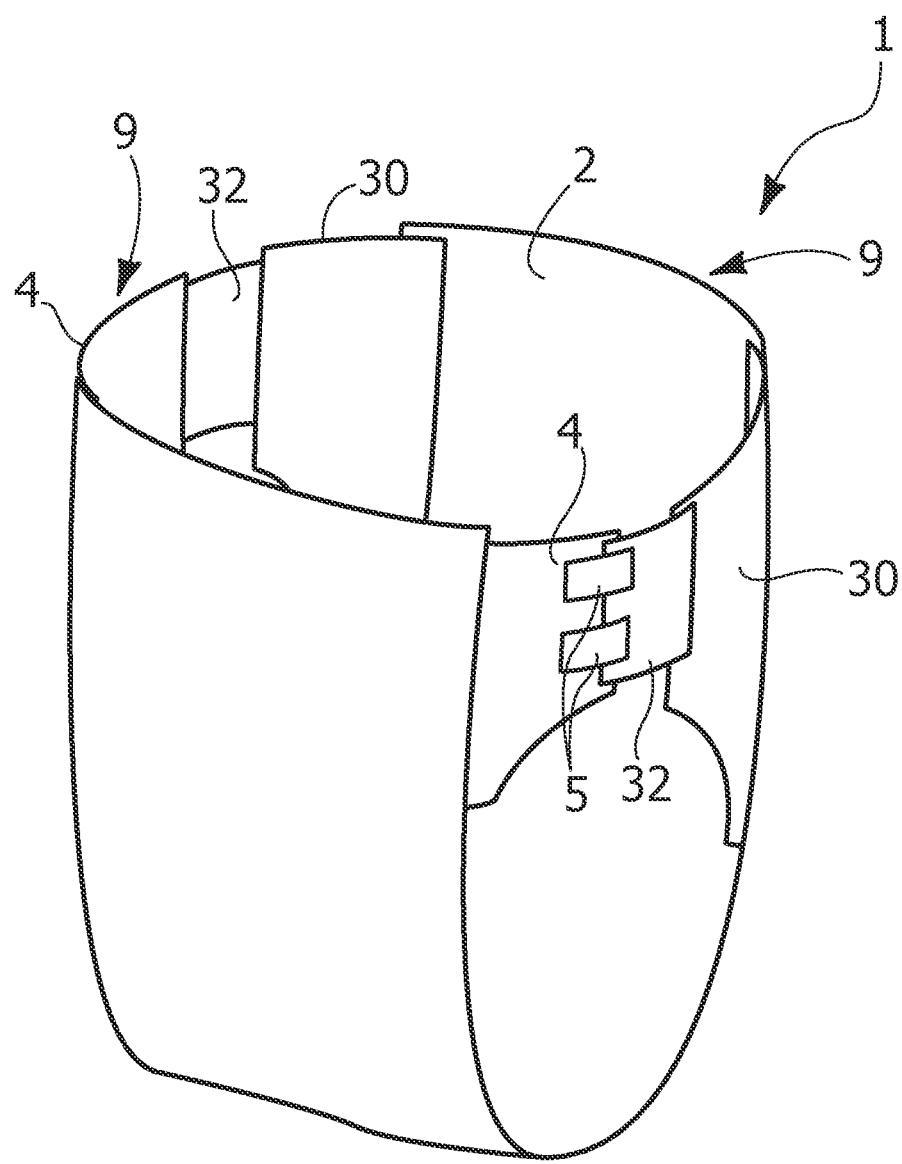

FIGS. 5 to 12 further illustrate the execution of various steps of a process according to one embodiment; and FIG. 13 illustrates an example of sanitary article according to one embodiment, represented in a closed position.

DETAILED DESCRIPTION OF EMBODIMENTS

Illustrated in the ensuing description are various specific details aimed at an in-depth understanding of the embodiments. The embodiments can be produced without one or more of the specific details, or with other methods, components, materials, etc. In other cases, known structures, materials or operations are not illustrated or described in detail herein so as not to render various aspects of the embodiments obscure.

The reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in different points of the present description, do not necessarily refer to one and the same embodiment. Furthermore, particular conformations, structures, or characteristics can be adequately combined in one or more embodiments.

The references used herein are provided merely for convenience and hence do not define the sphere of protection or the scope of the embodiments.

In particular, as used herein, expressions such as "connect, connected" refer to the joining, connection, attachment, sealing, etc. of two elements. Two elements are herein considered connected together when they are joined together directly or indirectly in a permanent way, as in the case where each element is directly connected to intermediate elements.

Figure 1:
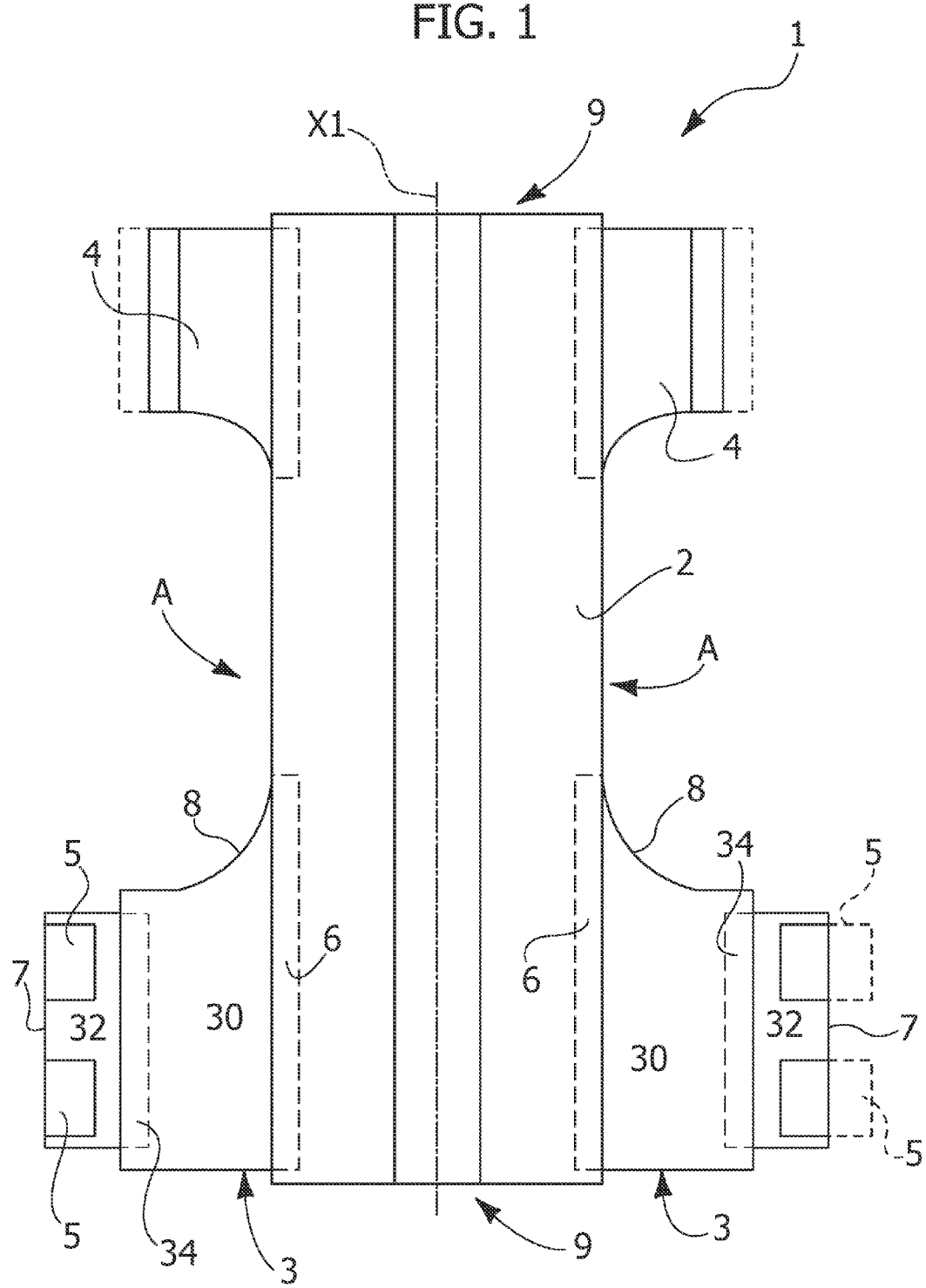
FIGS. 1 and 2 illustrate an example of sanitary article according to one embodiment, represented in an unfolded position and stretched out.

FIG. 1 of the annexed drawings is a schematic representation of a sanitary article 1 that can be worn as a pair of pants. By way of reference, and without any intention of limiting the possible sphere of application, the article 1 can be an absorbent article for incontinent adults.

The article 1 is represented herein in a condition where it is unfolded and stretched out in a plane and, according to a general configuration in itself known, comprises:
  a central body 2 (which, as will emerge more clearly in what follows, can be constituted by a topsheet permeable to liquids and by an impermeable backsheet, which are joined together with interposition of an absorbent structure), which can be set according to a general concave conformation around the crotch region of the user: the central body 2 extends in a longitudinal direction (main longitudinal axis X1 of the article 1) between two opposite ends;
  two (first) side panels 3 extending laterally on opposite sides from one of the ends of the central body 2; and
  two (second) side panels 4 extending laterally on opposite sides from the other end of the central body 2.

The side panels 3, 4 are connected to the central body 2 and are to define the waistband 9 of the article 1 when the latter is worn as a pair of pants, as may be appreciated more fully from FIG. 13.

In various embodiments the main body 2 can comprise:
  a so-called topsheet permeable to body fluids, which is to come into contact with the body of the user;
  a so-called backsheet, which is to be positioned towards the outside of the article, i.e., in contact with the garments of the user; and
  an element of absorbent material (core) set between the topsheet and the backsheet, which can be connected to one another with adhesive.

The article 1 can be worn with the main body or central body 2 wrapped to form a U around the crotch region of the user, with the end from which the side panels 4 extend situated on the front of the user and the end from which the side panels 3 extend set in a position corresponding to the small of the back of the user.

The side panels 3 can then extend on the sides of the user so as to be connectable, for example, via adhesive formations 5 or hook-and-loop formations (commonly referred to as "Velcro") to the side panels 4.

In various embodiments, the side panels 4 may be absent, and in this case the side panels 3 are connected directly to the front end of the central body 2.

Again, the relative position of the side panels 3 and of the side panels 4 can be reversed and, in this perspective, the terms "front" and "rear" are used herein only to distinguish the two pairs of side panels 3, 4 (if both are present), without this being understood as in any way limiting the modalities with which the article 1 is worn.

As has already been said, the side panels 4 may even be absent, in which case the distal edges of the side panels 3 are to be connected to the end of the central body 2 opposite thereto and, even though this solution is seldom adopted, the side panels 3 could be localized at the end of the central body that is to be set on the front of the user.

Furthermore, in the case of sanitary articles of the prefastened type it is envisaged that the article is packaged and made available to the user in a closed condition, i.e., with the side panels 3 (and 4, if present) already connected along the waistband of the article 1 according to the same arrangement illustrated in FIG. 13.

In the same way, as is well known to persons skilled in the sector, in addition to the aforesaid elements explicitly indicated herein, the article 1 can comprise numerous accessory elements, such as elastication elements, layers for acquisition of body fluids (the so-called "acquisition layers"), lateral formations for containing faeces (the so-called "cuffs"), etc. This applies also as regards the details of embodiment of the topsheet, of the backsheet, and of the absorbent core, which can be produced according to a practically infinite range of possible embodiments amply documented in the literature, including patent literature.

As has already been said, the connection formations 5 can be of an adhesive type or else produced so as to make a microhook or hook-and-loop (Velcro) connection with the panels 4 (or with the central body 2, in the absence of the panels 4) whether on account of the presence of complementary formations (not illustrated) on the panels 4 or on the surface of the body 2 or simply by exploiting, for the purposes of the microhook connection, the loop formations constituted by fibres provided by the outer layer of the panels 4 or else of the body 2.

Figure 2:
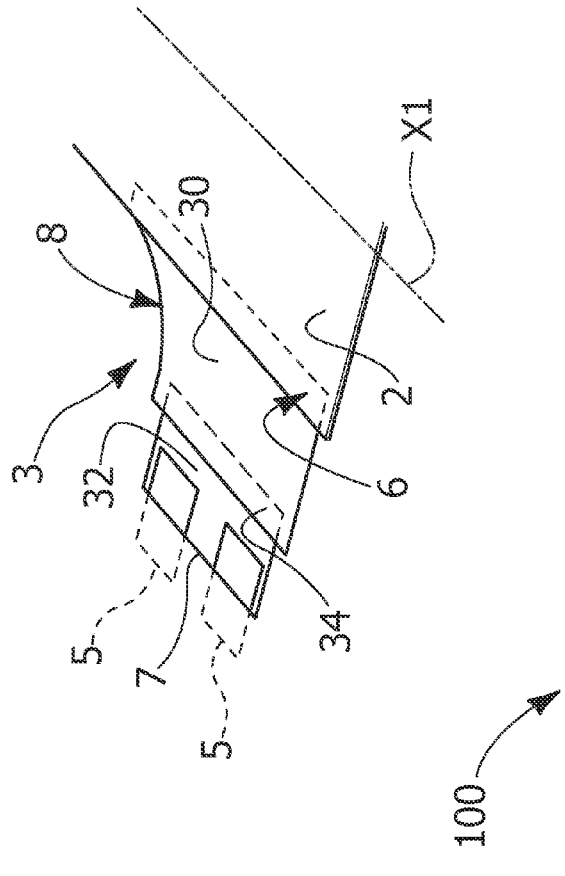

The sequel of the present description will for simplicity of exposition refer to connection formations 5 constituted by systems of connection or "labels" of an adhesive type initially turned over towards the inside of the side panels and then designed during use to be unfolded outwards (see the representation with a dashed line in the right-hand part of FIG. 1 or in FIG. 2) so that they can be applied against the outer surface of the side panels 4 (if present) or on the surface of the opposite end of the central body 2.

It will be noted that the individual panels 3 (and 4, if present) are to be applied in pairs of "twin" elements connected to opposite sides of the main body 2 in a condition of specular symmetry with respect to the main longitudinal axis X1 of the article 1.

In various examples of embodiment considered herein, the panels 3 have a tapered conformation, of which the proximal edges 6 and distal edges 7 form, respectively, the major base and the minor base. In the example of embodiment considered herein, the aforesaid tapered conformation envisages the presence of:
  an "outer" side (i.e., facing the outside of the article 1) of the approximately rectilinear configuration, orthogonal to the longitudinal axis X1; and
  an "inner" side (which faces the inside of the article 1 and is hence to define part of the boundary of one of the openings A provided for passage of the user's legs), which is also oriented in a direction as a whole transverse to the longitudinal axis X1 and comprises a curved proximal stretch 8 and a rectilinear distal stretch, which is orthogonal to the longitudinal axis X1.

In the example of embodiment considered herein, what has been said above applies substantially also to the side panels 4.

Possible other configurations of the panels 3 (and 4) can be inferred from EP-A-1 941 853 or from some of the documents cited in the corresponding research report.

FIG. 2 illustrates in greater detail the structure of the side panels 3 according to various embodiments, in which each panel 3 comprises:

an internal portion 30, connected to the central body 2 at the proximal edge 6; and an external portion 32, which carries the closing means 5 (adhesive formations, formations of a hook-and/or-loop type, etc.).

The internal portion 30 and the external portion 32 are connected together along an intermediate region 34 of the panel 3.

The internal portion 30 can be fixed to the central body 2 according to any of the techniques commonly used for fixing the side panels 3 (or 4) to the central body 2 of an article 1 of the type considered herein.

For instance, in various embodiments, the proximal edge 6 of the internal region 30 can be set between the topsheet and the backsheet of the central body 2 and fixed thereto with different techniques, such as gluing, heat-sealing, ultrasound sealing (possibly used in a combined way, for example, by gluing to either one between the backsheet and the topsheet and heat-sealing or ultrasound sealing to the other between the backsheet and the topsheet).

Similar considerations apply to the connection of the internal portion 30 and of the external portion 32 in the region 34, which, as may be appreciated in the figures, has an elongated shape aligned to the direction of the main axis X1 of the article 1.

In various embodiments, the internal region 30 and the region 32 can differ from one another both as regards the shape and as regards the materials used for their production.

As regards the shape, in the example of embodiment considered herein, the external portion 32 has a rectangular shape, in which it is in general possible to distinguish two sides with rectilinear configuration, oriented in a direction orthogonal to the longitudinal axis X1, hence to the distal edge 7 of the panel 3, said sides being, respectively, external and internal if reference is made to the general arrangement with respect to the development of the article 1.

In various embodiments, the internal portion 30 has an outer side with respect to the article that has the rectilinear configuration substantially aligned to the outer side of the external portion 32, hence with orientation orthogonal to the longitudinal axis X1 and hence to the distal edge 7. The inner side 8 of the portion 30 (also in this case the terms "outer side" and "inner side" refer to the general arrangement with respect to the development of the article 1) has, instead, a curved configuration corresponding to the generically arched boundary that it is intended to impart on the openings A of the article 1 provided for the passage of the user's legs.

As regards the materials, in various embodiments the internal region 30 can be produced with a nonwoven-fabric material of the type widely used in the manufacture of sanitary articles, and the outer region 32 can be made of a similar material.

In various embodiments, the outer region 32 can present characteristics of extensibility of an elastic type, being obtained, for instance, with the solution described in the document No. U.S. Pat. No. 6,572,595 or the document No. U.S. Pat. No. 6,994,761, so as to present also characteristics of "breathability".

The closing formations 5 can be connected to the external portion 32 of the panels 3 with different solutions in themselves known, for example, according to the characteristics of the formations 5 themselves. For instance, in the case of formations in the form of adhesive labels, it is possible to, resort to one of the numerous solutions documented in the literature, also at a patent level, for application of the adhesive closing formations of the most widely used sanitary articles. In the case where the formations 5 are constituted by elements of a hook-and/or-loop type or a microhook closing type, it is possible to apply said formations on the panel 3 via adhesive.

Figure 3:
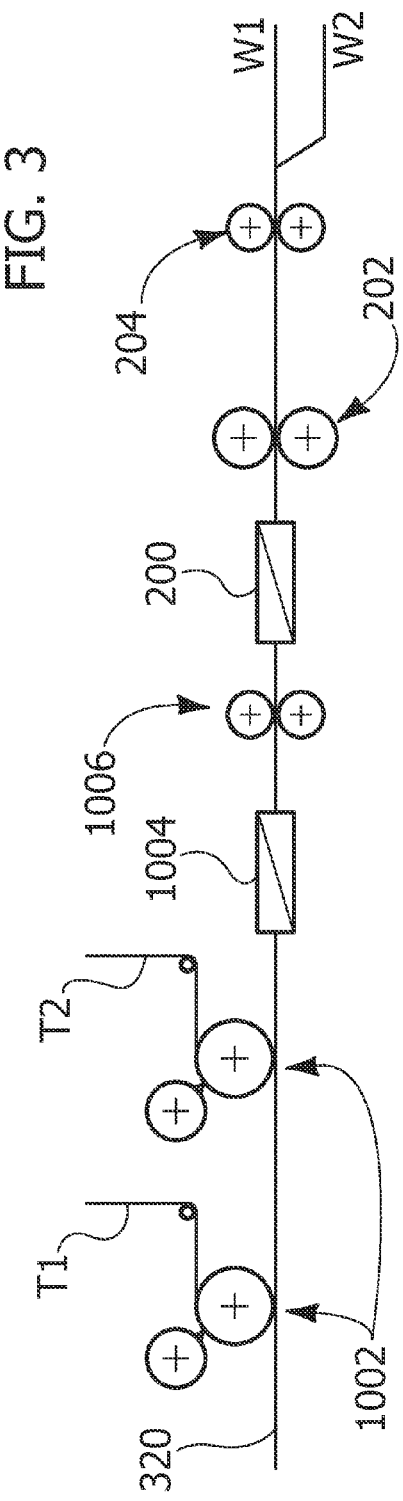
FIGS. 3 and 4 illustrate successive steps of a process according to one embodiment.
Figure 4:
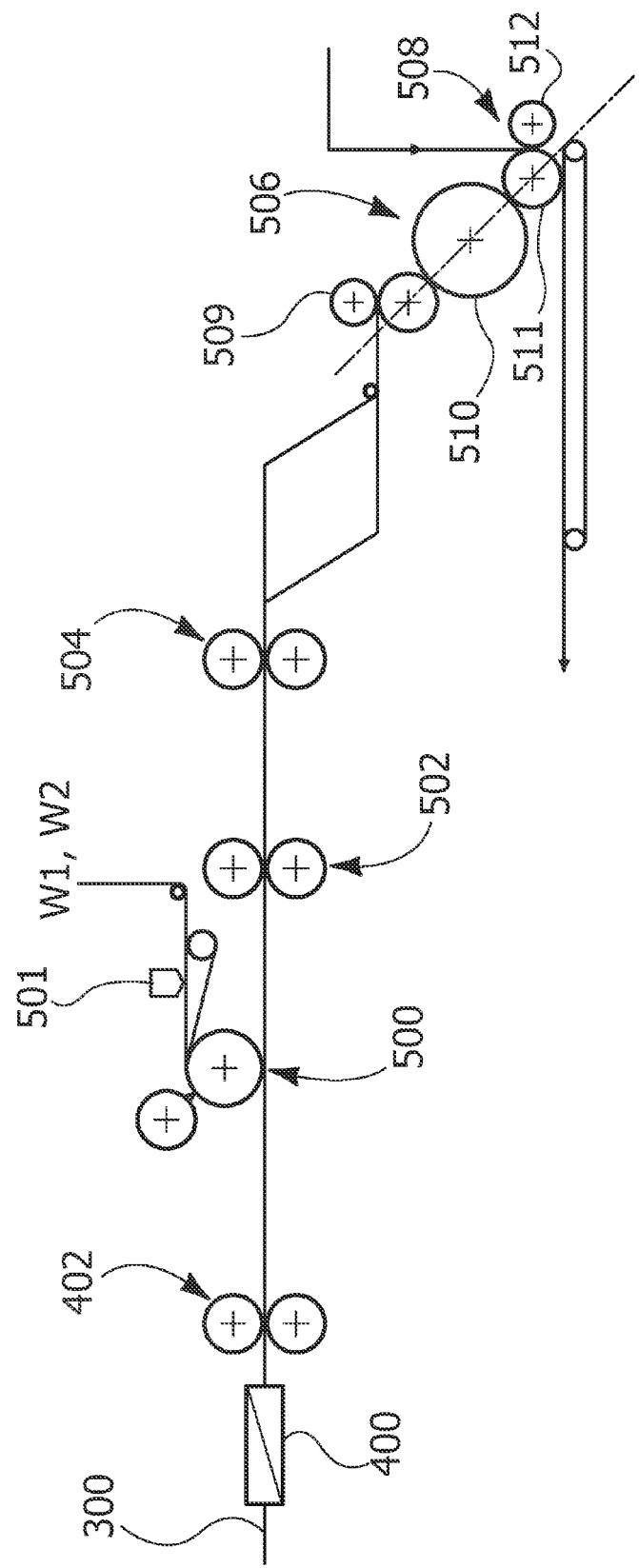

FIGS. 3 and 4 illustrate schematically the layout of a production plant and consequently a possible sequence of operations of treatment to which it is possible to resort for producing an article 1 of the type illustrated in the figures. In this regard, it will be appreciated that the individual steps of treatment and the corresponding equipment mentioned with reference to FIGS. 3 and 4 correspond to technical solutions to be deemed in themselves individually known, which renders superfluous any further detailed description thereof herein.

FIG. 3 regards a sequence of operations to which it is possible to resort in order to provide the external portions 32 of the panels 3.

In the diagram of FIG. 3, the reference 100 designates as a whole a station in which applied on a web 320, for example, of nonwoven fabric, i.e., of an elasticated and/or "breathable" material, as described for instance, in the documents Nos. U.S. Pat. No. 6,572,595 or U.S. Pat. No. 6,994,761, already cited previously, are the closing formations 5 of the type already described previously (adhesive, microhook means, etc.).

The application of said formations 5 is made according to criteria in themselves known, which do not require any further detailed description herein. In the case where a (non-limiting) example of formations 5 in the form of adhesive formations is considered, said formations can be applied on the opposite sides of the web 320 that advances along an axis X320 via two stations of application 1002 (for example, of the "cut & slip" type), which receive web material T1, T2 constituting the formations 5 from supply reels (not visible in the drawings), apply adhesive thereon, and segment the aforesaid web material to form the individual formations, which are then applied aligned to one another (or staggered) with a desired application pitch on opposite sides of the web 320. Said application pitch is chosen, for instance, according to the fact that in an article 1 of quite considerable dimensions, on the distal edge 7 of the side panels 3, there can be applied not just one but a number of closing formations 5 (for example, two in number in the example illustrated herein).

It will be appreciated that, even though they are represented staggered in the left-hand part of FIG. 3, the two stations 1002 can be in effect set in pairs in positions specularly symmetrical with respect to the central axis X320 of the web 320.

Downstream of the stations 1002, the web 320 that has received the formations 5 advances towards a folding device 1004, which completes the operation of application of the formations 5 by re-folding the formations 5 themselves according to a general V-shaped configuration so as to bring them to embrace the opposite sides of the web 320. This is the folded condition starting from which the formations 5 can then be unfolded (see the representation with a dashed line, for example, in FIGS. 1 and 2) to perform their function. The connection of the formations 5 on the opposite sides of the web 320 is then reinforced by an operation of pressing performed in a pressing station 1006.

It will be appreciated that FIGS. 3 to 11 attached hereto refer to an example of a sequence of operations that are to be performed in a condition of substantial symmetry so as to generate and apply simultaneously on opposite sides of the central body 2 two side panels 3 (and two side panels 4). This solution presents characteristics of evident functionality from the standpoint of implementation but must not on the other hand be considered of an imperative nature, in the sense that all the operations described herein could in themselves be performed independently even on just one side of the panel of the central body 2.

Once again it is recalled that the modalities of formation and application of the closing formations 5 on the outer parts 32 of the side panels 3 are in general dictated by the characteristics of the closing formations used. For instance, in the case where the closing formations 5 are formations of a hook-and/or-loop type of a microhook closing means, the station 100 will not comprise the folding device 1004 and may possibly do without even the pressing unit 1006.

Located downstream of the station for application of the closing formations 5 (station designated as a whole by 100 and comprising the devices designated by 1002, 1004 and 1006) is a folding device 200 (of a known type), the function of which is that of imparting on the web 320 that continues to advance along the axis X320 a general C-shaped configuration such as to bring the external edges of the web 320 with the closing formations 5 applied thereon to be turned over in 321 (FIG. 6) according to a general V-shaped configuration towards the median axis X320 of the web 320. This folded configuration is maintained subsequently by the web 320 and by the external portions 32 that are to be obtained therefrom according to the modalities described more clearly in what follows.

Downstream of the folding device 200 a unit 202 can be set with the function of providing between each of the external edges of the web 320 folded in 321 towards the median axis X320 and the central part of the web 320 an action of sealing such as to cause the web 320 (and the portions 32 subsequently obtained therefrom) to maintain the same folded configuration subsequently.

For this purpose, the unit 202 can carry out (according to known criteria) a so-called "technical sealing" implemented, for instance, via a relatively bland action of heat-sealing or ultrasound sealing, or else via the application of a so-called "green" glue. Adhesives that are able to perform such a technical-sealing function are comprised, for example, in the production of the firm Savare of Milan.

Figure 6:
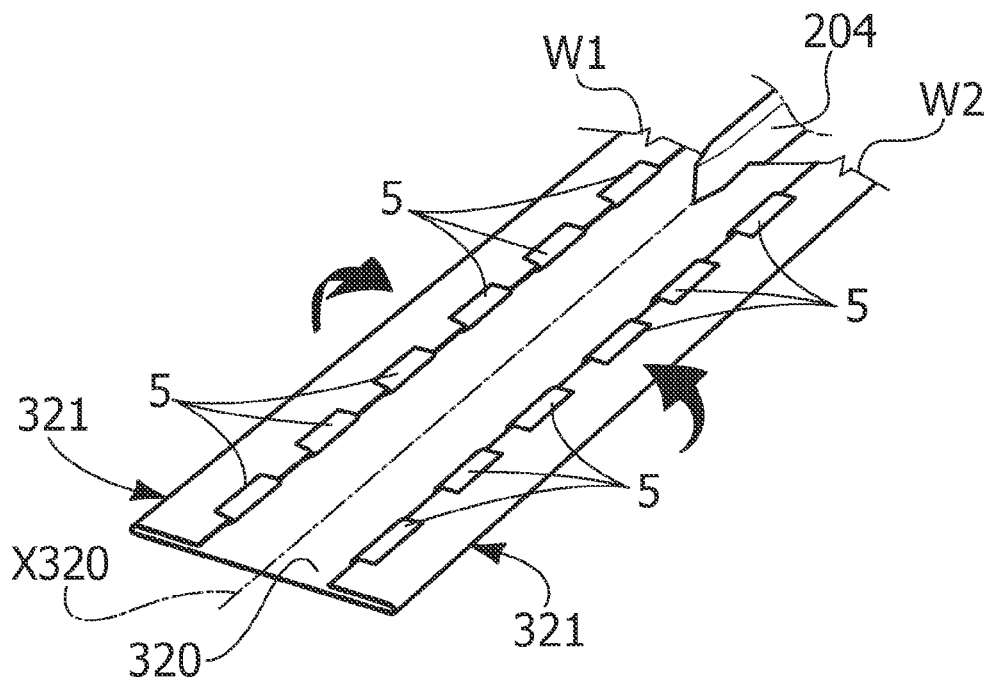

In the right-hand part of FIG. 3, the reference 204 then designates a cutting unit (for example, a cutter with vertical blade—see the right-hand part of FIG. 6), which, by operating along the axis X320 of the web 320, divides the aforesaid folded web C in the station 200 into two sub-webs, designated, respectively, by W1 and W2.

Each of the webs W1 and W2 is to give rise, according to the modalities described more fully in what follows, to the external portions 32 of the side panels 3 that are to be applied on one side of the central body 2.

FIG. 4 is a schematic illustration of a sequence of operations that lead in the first place to the formation of the internal parts 30 of the side panels 3 (and, in the non-limiting example of embodiment illustrated herein, to the panels 4).

Figure 7:
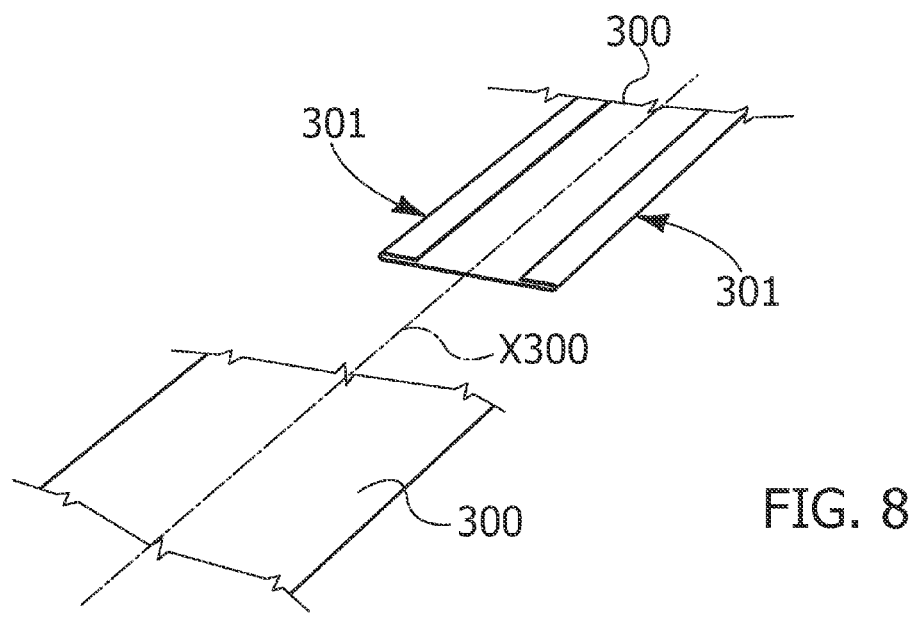

Starting from a web 300, for instance, of a material such as a nonwoven fabric, which advances along its longitudinal axis X300, in a folding station 400 a general C-shaped configuration is imparted on the web 300 by turning over the external edges of the web 300, towards the aforesaid axis X300 according to a general V-shaped configuration along folding lines 301 (end pleat) (see FIG. 7).

In a station 402 substantially similar to the station 202, the C-shaped fold of the web 300 along the folding lines 301 is stabilised with a technical sealing (bland heat-sealing/ultrasound sealing or application of "green" glue) in such a way that the web 300 maintains the folded C-shaped configuration during the subsequent operations of treatment described in what follows.

Figure 5:
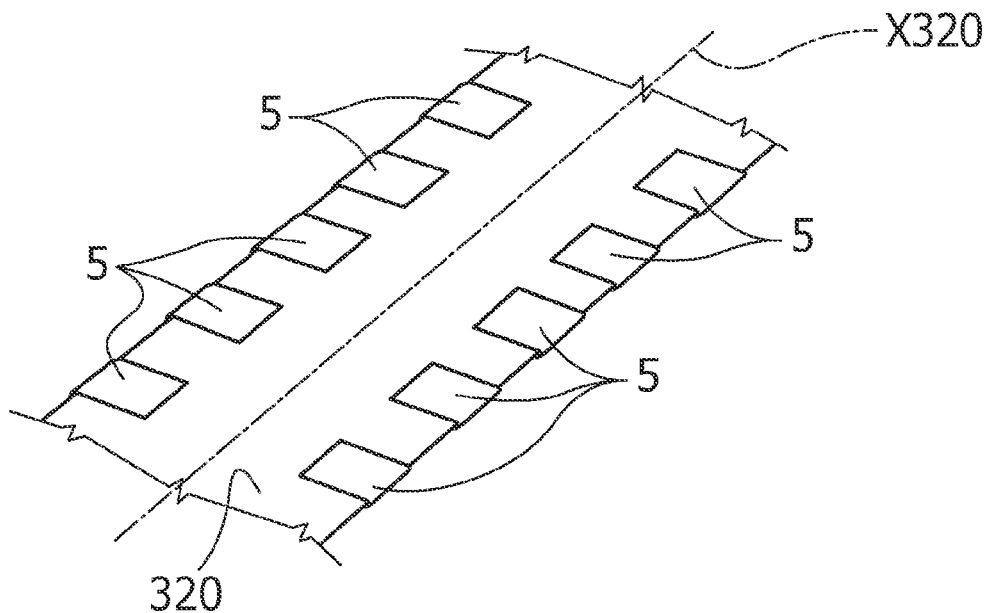

The reference 500 designates an application station 500 (for example, of the cut-&-slip type), which, in addition to the web 300, receives also the two webs W1 and W2, the formation of which has been previously described with reference to FIG. 3 and to the sequence of FIGS. 5 and 6.

Figure 8:
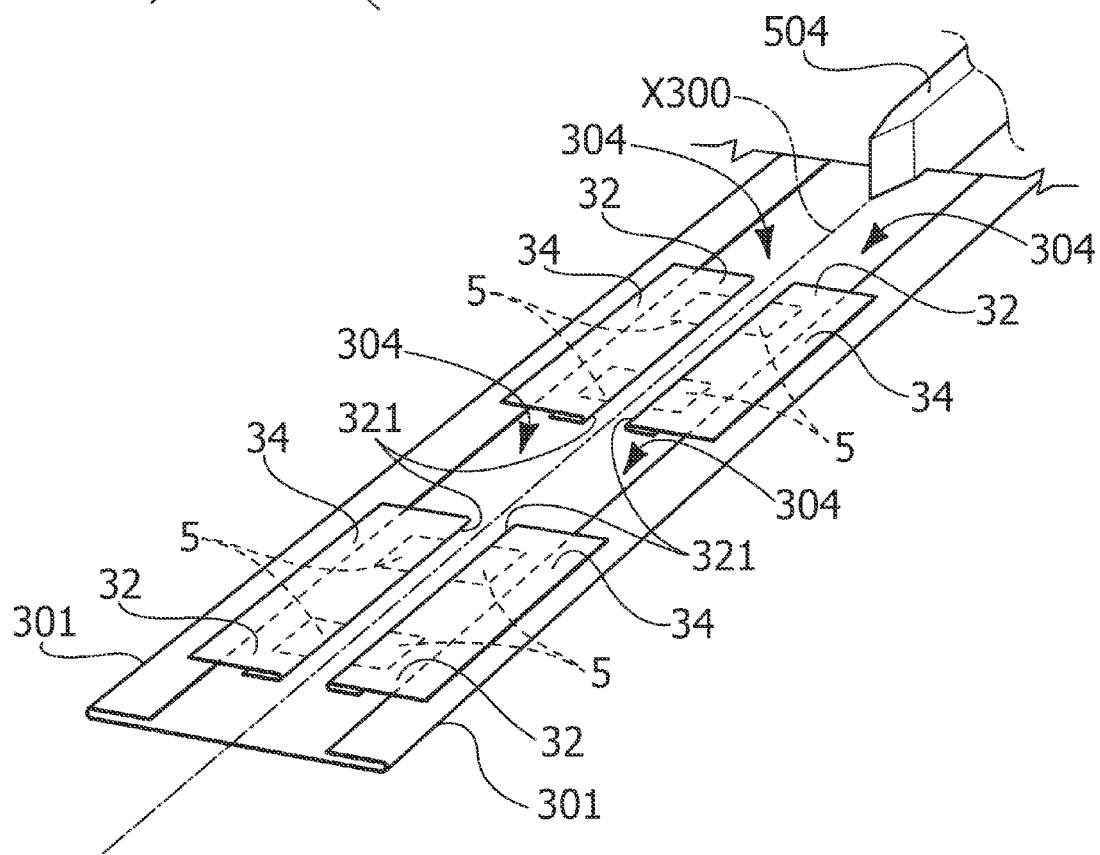

As schematically represented in FIG. 8, the station 500 applies—on the side of the web 300 on which in 301 the external edges of the web itself are turned over—lengths of the two webs W1 and W2 oriented in such a way that the folding lines 321 formed in the unit 200 face the centre line (longitudinal axis) X300 of the web, whilst the "straight" (i.e., non-folded) edges of the two webs W1 and W2, corresponding to the action of cutting performed by the unit 204 at the axis X320, face the edges of the web 300 folded along the lines 301.

As more clearly illustrated in FIG. 4, associated to the device 500 is a station for applying glue 501, which enables spreading of strips of adhesive on the webs W1 and W2 at the external edges of the webs W1 and W2, in other words at the edges generated by the action of cutting performed with the unit 204. This adhesive seals the external edges of the web 300 (folded along the line 301) to the "straight" edges of the lengths of web W1 and W2 so as to give rise to the regions of connection 34 that are to connect together the internal portion 30 and the external portion 32 of each side panel 3.

In various embodiments, the lengths of web W1 and W2 are applied not contiguous to one another, but leaving, instead, between two successive lengths (and this explains why in various embodiments the station 500 is a station of a cut-&-slip type, such as to enable relative sliding of the lengths of web W1 and W2 with respect to the web 300 that advances along the axis X300) a free stretch 304, which, as will be appreciated more fully in what follows, enables production of the panels 4. Of course, in various embodiments in which the panels 4 are not envisaged, the application of the lengths of web W1 and W2 on the web 300 can be made in positions that are even strictly contiguous.

Downstream of the station 500 there may be present a station 502 (once again, as in the case of the stations 202 and 402, this may be a heat-sealing/ultrasound-sealing station or a station for application of "green" glue), which carries out a technical sealing, establishing a connection between the edges of the lengths of web W1, W2 folded along the lines 321 with the central part of the web 300, preventing undesirable accidental unfolding of the ensemble just formed.

There is then present a further station for longitudinal cutting 504, such as a cutter (at the top of FIG. 8), designed to act along the median longitudinal axis X300 of the web 300 so as to divide into two the web itself, on which the lengths of web W1 and W2 that define the external portions 32 of the side panels are applied.

The two sub-webs thus formed are fed to a station 506, which is entrusted with a dual function:

sectioning/segmentation into successive lengths the two half-webs obtained from the web 300, which carries applied thereon the external portions 32, with a cutting station 509; and application of said lengths on the opposite sides of the central body 2, according to the typical modalities of manufacture of sanitary articles produced in the form of a chain of articles that are to be separated from one another with an operation of longitudinal cutting implemented after completion of the formation of the articles themselves, by means of an operation of repitching performed with a repitching unit 510 and an operation of sealing to the central body 2 (or to a portion thereof) with a sealing unit 508.

The sequence of FIGS. 9 and 10 refers to the production of articles 1, in which (also) the side panels 4 are present.

Consequently, the segmentation of the (half)webs in question occurs according to lines of transverse cutting a and b that are designed:

in the case of the lines a, to separate a length of (half)web with an external length/portion 32 of panel 3 applied thereon from a stretch 304 of the same (half)web that has the original configuration in so far as it is designed to form the side panels 4; and in the case of the lines b, to separate a stretch of (half)web that has the original configuration from a length of (half) web with an external length/portion 32 of panel 3 applied thereon.

In the case where the panels 4 are not envisaged, the operation of segmentation is performed between successive portions of (half)web, on which respective lengths of web W1 and W2 are applied, which form respective external portions 32.

In addition to the operation of segmentation of the web 300, within the station 506 there is performed also an operation of repitching of the lengths thus obtained such as to lead to the application on the central body 2 of the successive lengths of web applied in conditions where they are set apart from one another.

In various embodiments, on each stretch of central body 2 that is to correspond to one of the articles 1 there can be applied, on each of the two sides of the central body 2:

a first length of (half)web 300, which corresponds to a stretch 304 and is to form one of the front panels 4; said length is applied at the stretch of the central body 2 that is to define one of the ends (for instance, the front end) of the article 1; and a second length of (half)web 300, which carries an external portion 32 applied thereon and is to form one of the rear panels 3; said length is applied at the stretch of the central body 2 that is to define the other end (for instance, the rear end) of the article 1.

In various embodiments, it is also possible to consider performing the operations of cutting along the lines a and b one after the other, performing first just one of said cutting operations (for example, the one along the line b) and applying, on each side of the central body 2, after repitching, hence with a pitch equal to the length of the articles 1 that it is desired to produce, lengths of web 30 comprising:

a first part of length of (half)web 300, which carries an external portion 32 applied thereon and is to form one of the rear panels 3; and a second part of length of (half)web 300, which corresponds to a stretch 304 and is to form one of the front panels 4.

The next further cutting operation (with reference to the example considered herein, i.e., the one along the lines a), which can be obtained using the same blade that segments the individual articles 1 (final cutting), separates the two parts of length in question, thus separating, on each side of the central body 2, the rear panel 3 of a first article 1 and the front panel 4 of an adjacent article in the production line of the articles 1.

It will be appreciated that the sequence of performance of the cutting operations (first line b and then line a, or else first line a and then line b) depends upon whether it is desired to come out with the individual articles 1 from the production line with the panels 4 before the panels 3 or else with the panels 3 before the panels 4.

Whatever the embodiments, the openings A provided for passage of the user's legs are as a whole defined already just as a result of the spacing of the lengths of web formed in the station 506, without generating waste of any sort or with an extremely contained generation of waste S.

FIG. 11 highlights the fact that, in various embodiments, it is envisaged to bestow upon the internal sides 30 of the side panels 3 (and of the panels 4, if present) a curved (or, in general "anatomic") profile, with an action that leads to the waste of just a small amount (designated by S in FIG. 11) of material.

This operation can be performed once the panels 3 (and 4) have been applied on the central body 2. In various embodiments, it is, however, possible to envisage that the aforesaid curved profile will be bestowed by the blade that is to perform the cut along the line of cut b (for example in the station 509), for instance, thanks to the fact that said blade has a conformation characterized in that it has two arched cutting edges joined to a third blade perpendicular to the edges 301 and to the edges generated by the cutter 504.

In various embodiments, wherever the aforesaid cut according to a curved profile is made, it is obtained in such a way that:

in the case of the panels 3, the cut involves only the internal portion 30; and both in the case of the internal portion 30 of the panels 3 and in the case of the panels 4 (if present), the curved cut involves only the proximal stretch, whereas in the distal stretch, where the flap folded according to the line 301 is present, the cut is a rectilinear cut orthogonal to the main axis X1 (hence to the edges of the central body 2) so as to prevent shapes that may be bothersome such as, for instance, sharp edges facing the inside of the opening A for the legs.

The fact that the cut (and the consequent generation of waste) can concern only the internal portion 30 of the side panel 3, excluding the external portion 32 from cutting, is particularly appreciable in the case where the material constituting the external portions 32 is an elasticated material and/or material with features of "breathability": at least at the moment, this material is considered a material of rather high quality, of which it is desired to minimize the amount of the waste. Various embodiments hence enable total elimination of the waste of this material.

According to known criteria, the application of the lengths of (half)web that form the internal portions 30 and carry the external portions 32 is usually made before the central body 2 of the article 1 is completed as regards its formation.

For instance, in various embodiments, the lengths in question are applied on the central body 2 when the latter comprises only one of its external films (for example, the backsheet) with possibly applied thereon—if envisaged—the cores that bestow characteristics of absorbency on the articles 1. For instance, in FIG. 11 the panels 3 and 4 have their proximal edges still left partially uncovered by the central body 2. The completion of the central body (for example, the application of the cores—if they have not already been applied previously—and the application of the topsheet) can be carried out in the finishing station 508 downstream of which, according to known criteria, the chain of articles 1 thus formed is sent on to a station for transverse segmentation, which is to obtain, from the chain of articles, the individual articles 1, which have the characteristics represented schematically in FIG. 12.

In any case, it will be appreciated that the side panels 3 are connected to the central body 2, whilst the panels 3 are in a folded condition. Rather, as has been seen, the aforesaid panels are produced (i.e., "formed") in a folded condition, by applying the portions 30 and 31 against one another with the distal edge 7 set in the proximity of the proximal edge 6.

Various embodiments enable execution of various operations of production and of manipulation of the article 1 to be rendered less critical, also as regards subsequent packaging thereof.

For instance, since the panels 3 are applied to the central body 2 in a folded condition (after being in effect manufactured in a folded condition), an article 1 that has, in the totally unfolded configuration of FIG. 1, a width (distance between the distal edges 7 of the panels 3) of, for example, 82 cm can present, in the final condition of manufacture of FIG. 12, a width of just 59 cm. It will be appreciated that said reduction in width involves also the front panels 4 (if present), which are also connected to the central body 2 with their distal edge folded (in 301, FIG. 7).

As schematically illustrated with a dashed line in the top part of FIG. 1, the distal edge of the panels 4 can be unfolded (by overcoming the resistance exerted by the "technical" connection obtained in the station 400 of FIG. 4) so as to widen further the waistband of the article 1, thus enabling the article as it is worn to be rendered optionally larger. At the same time, by keeping the panels 4 in a folded condition, i.e., preventing complete unfolding of the distal edges, folded in 301, it is possible to wear the article so that it is more adherent, without giving rise to formations such as to prove troublesome for the person wearing the article.

Finally, the possible waste of material is minimized and in effect limited to the "anatomic" shaping of the edges of the openings A for the passage the user's legs and not to the formation of said openings as a whole.

Of course, without prejudice to the principle of the invention, the details of production and the embodiments may vary even significantly, with respect to what is illustrated herein purely by way of non-limiting example, without thereby departing from the scope of the invention as defined by the annexed claims. In particular, whilst the description provided by way of example herein regards the mass production of articles according to the "machine direction" (MD) mode, i.e., with the articles being formed that advance in the direction of their longitudinal axis X1, various embodiments are suited to the mass production of articles according to the "cross direction" (CD) mode, i.e., with the articles being formed that advance with their longitudinal axis X1 oriented crosswise with respect to the direction of advance.

Again, whilst the examples illustrated herein envisage connecting the side panels 3 to the central body 2 in a condition folded like a book towards the inside of the article 1 (i.e., with the fold 301 made so as to overturn the external edge of the portion 30 on the surface of the portion 30 that is to face the inside of the article 1, i.e., to face the body of the user), various embodiments could envisage that the fold 301 is made in an opposite direction, towards the outside of the article 1 (i.e., downwards, as viewed in FIGS. 9 and 10), in which case the side panels 3 would be connected to the central body 2 in a condition folded like a book towards the outside of the article 1.

The examples illustrated herein envisage, in the framework of the individual panel 3, making the connection (in the region 34) between the internal portion 30 and the external portion 32 by folding (along the line 301) the material constituting the internal portion 30 on itself. In various embodiments it is possible to adopt a complementary solution, providing the connection (in the region 34) between the internal portion 30 and the external portion 32 folding the material constituting the external portion 30 on itself so that, when it is applied on the internal portion 30, at this point without the fold 301, the external portion 32 has, in addition to the fold 321 (the presence of which is not on the other hand imperative) on its side that faces the axis X1, a homologous fold, which is specularly symmetrical, on its side that is to be opposite to the axis X1. All these embodiments and equivalent embodiments implement the solution of producing the side panels 3 and connecting them to the central body 2 in a folded condition, whereas the solutions that are today most widespread envisage producing the side panels 3 and connecting them to the central body 2 in a plane unfolded condition and folding them only after their connection to the central body 2.

The invention claimed is:

1. A method of producing a sanitary article wearable as pants, the article including:
   a central body to be arranged around the crotch portion of the user, said central body extending in a longitudinal direction between two opposed ends, and
   at least one pair of side panels connected to one of the ends of said central body and extending from opposite sides of said central body to define at least a portion of a waist line of the article, the side panels of said at least one pair having each a proximal edge connected to said central body and a distal edge carrying closure formations for the article at its waist line,
   wherein the method comprises:
   producing said central body,
   producing said at least one pair of side panels, and
   connecting the side panels of said at least one pair of side panels to said central body with said side panels in a folded condition,
   wherein the method also comprises:
   i) producing the side panels, of said at least one pair in a folded condition by providing:
   an inner portion to connect to said central body at said proximal edge, and
   an outer portion carrying a closure means at said distal edge said inner portion and said outer portion being connectable to each other at an intermediate region of the respective side panels,
   ii) folding over one of said inner portion and said outer portion to form an end pleat at said intermediate region,
   iii) applying said outer portion against said inner portion by connecting them via said end pleat at said intermediate region, and
   iv) connecting said inner portion to said central body at said proximal edge, whereby the side panels of said at least one pair are connected to said central body in a folded condition.

2. The method of claim 1, wherein, in said folded condition, said side panels have their distal edge in proximity of said proximal edge.

3. The method of claim 1, including folding over said inner portion at said intermediate region by forming said end pleat.

4. The method of claim 1, including folding over said outer portion at said distal edge.

5. The method of claim 1, including:
   producing said inner portion in the form of a continuous web having connected thereto the outer portions of a plurality of respective side panels, subjecting said continuous web to segmentation to form stubs each to produce one of said side panels of said at least one pair.

6. The method of claim 1, wherein the side panels of said at least one pair have an inner side with respect to the longitudinal direction of the article, the method including providing at said inner side a shaping cut for one of a side opening for a leg of a user of the article.

7. The method of claim 1, including making a shaping cut exclusively at said inner portion, whereby the outer portion connected thereto is not cut during the shaping cut.

8. The method of claim 1, including connecting to said central body a further pair of side panels connected to the end of said central body opposed to the end to which said at least one pair of side panels is connected, the panels of said further pair having an end pleat at the respective distal edge.

9. The method of claim 5, including:
   leaving, in said continuous web, separation zones between said inner portions connected to said continuous web, and
   producing the side panels of said further pair from said separation zones left in said continuous web.

10. The method of claim 8, wherein the side panels of said further pair have an inner side with respect to the longitudinal direction of the article, the method including providing at said inner side a shaping cut for one of a side opening for a leg of a user of the article.

11. The method of claim 6, wherein said shaping cut includes:
   a proximal curved section, and
   a rectilinear distal section, orthogonal to the main axis of the article, located at a pleat of the respective panel.

12. A sanitary article wearable as pants, including: a central body to be arranged around the crotch portion of the user, said central body extending in a longitudinal direction between two opposed ends, and at least one pair of side panels-connected to one of the ends of said central body and extending from opposite sides of said central body to define at least a portion of the waist line of the article, the side panels of said at least one pair each having a proximal edge connected to said central body and a distal edge having closure formations for the article at its waist line, wherein: i) the side panels of said at least one pair include an inner portion connected to said central body at said proximal edge and an outer portion carrying said closure means at said distal edge, said inner portion and said outer portion being connected to each other at an intermediate region of the respective side panel, ii) one of said inner portion and said outer portion is folded over at said intermediate region to form an end pleat, and iii) said outer portion is applied against said inner portion and connected thereto via said end pleat at said intermediate region.

13. The article of claim 12, wherein said end pleat is in said inner portion and is folded towards the inside of the article.

14. The article of claim 12, including a further pair of side panels connected to the end of said central body opposed to the end to which said at least one pair of side panels is connected, wherein the panels of said further pair include respective selectively deployable, folded over distal edges.

15. The method of claim 3, wherein said end pleat is folded towards the inside of the article.

16. The method of claim 4, wherein the folding over said outer portion at said distal edge occurs before connection to said inner portion at said intermediate region.

\* \* \* \* \*